(12) United States Patent
Krüger et al.

(10) Patent No.: US 6,968,843 B2
(45) Date of Patent: Nov. 29, 2005

(54) CLEARING MODES OF OPERATION OF MEDICAL ENGINEERING DEVICES

(75) Inventors: Thomas Krüger, Reinfeld (DE); Hartmut Schmidt, Heilshoop (DE); Hans-Georg Wahle, Reinfeld (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 418 days.

(21) Appl. No.: 10/079,604

(22) Filed: Feb. 20, 2002

(65) Prior Publication Data

US 2002/0144682 A1 Oct. 10, 2002

(30) Foreign Application Priority Data

Apr. 4, 2001 (DE) ................................. 101 16 650

(51) Int. Cl.⁷ .......................... A61M 16/00; A62B 7/00; F16K 31/02
(52) U.S. Cl. ........................ 128/204.21; 128/204.18; 128/200.24; 128/203.14
(58) Field of Search ....................... 128/204.18, 204.21, 128/204.23, 205.23, 200.24, 203.14

(56) References Cited

U.S. PATENT DOCUMENTS

| | | | |
|---|---|---|---|
| 4,464,172 A * | 8/1984 | Lichtenstein ................. | 604/65 |
| 4,984,158 A * | 1/1991 | Hillsman ................ | 128/200.14 |
| 5,560,353 A * | 10/1996 | Willemot et al. ...... | 128/204.21 |
| 5,915,379 A * | 6/1999 | Wallace et al. ........ | 128/204.21 |
| 5,931,160 A | 8/1999 | Gilmore et al. | |
| 6,158,432 A * | 12/2000 | Biondi et al. .......... | 128/204.21 |
| 6,463,930 B2 * | 10/2002 | Biondi et al. .......... | 128/204.21 |
| 6,578,575 B1 * | 6/2003 | Jonson .................. | 128/204.21 |
| 6,584,973 B1 * | 7/2003 | Biondi et al. .......... | 128/204.21 |

* cited by examiner

Primary Examiner—Henry Bennett
Assistant Examiner—Andrea M. Ragonese
(74) Attorney, Agent, or Firm—McGlew and Tuttle, P.C.

(57) ABSTRACT

A process and system are provided for clearing modes of operation of a medical engineering device, especially modes of operation on a respirator (1), such as IMV (Intermittent Mandatory Ventilation, CPAP (Continuous Positive Airway Pressure) or HFV (High-Frequency Ventilation). The clearing is performed with an external electronic, optical or magnetic storage medium, e.g., a chip card (2), on which data that determine the available modes of operation and optionally the duration of their availability are present. The data on the chip card (2) are read by a writing and reading unit (3) of the respirator (1). The data may be coded, the duration of availability of a mode of respiration may be controlled by keeping a time log (9) on the chip card, and the corresponding time periods are debited from the time log (9) each time a certain mode of operation is used.

15 Claims, 3 Drawing Sheets

US 6,968,843 B2

CLEARING MODES OF OPERATION OF MEDICAL ENGINEERING DEVICES

FIELD OF THE INVENTION

The present invention pertains to a process for clearing modes of operation of a medical engineering device. The modes of operation are functions which are already implemented in the software of a medical engineering device, especially a respirator, or can be implemented with software or otherwise. In the case of a respirator, a mode of operation corresponds, e.g., to a certain mode of operation such as IMV (Intermittent Mandatory Ventilation), CPAP (Continuous Positive Airway Pressure) or HFV (High-Frequency Ventilation).

BACKGROUND OF THE INVENTION

A device and a process for controlling a respirator are described in U.S. Pat. No. 5,931,160. The different modes of operation are performed or modified on the device according to rules set on the device before according to the user's specification.

The fact that the user must determine in advance what modes of operation shall be available to him at the time of the purchase is a drawback of the prior-art device. If the profile of requirements imposed on the device changes, i.e., additional modes of respiration are desired, and some modes of respiration are no longer necessary, the corresponding software modification with respect to the new profile of requirements must be performed on the device itself. This service can only be performed on site and is therefore associated with additional efforts and costs.

SUMMARY AND OBJECTS OF THE INVENTION

The object of the present invention is to provide a process with which the modes of operation available on a medical engineering device can be changed without a great technical effort.

According to the invention, a process for clearing modes of operation on a medical engineering device is provided with the following steps:

a) data that specify a number of different available modes of operation on the medical engineering device are read into an external electronic, optical or magnetic storage medium, b) the data are read by a writing and reading unit associated with the medical engineering device, c) the data read by the writing and reading unit determine the clearing of the available modes of operation on the medical engineering device.

The clearing of the modes of operation is performed such that data that specify a certain selection of different available modes of operation on the medical engineering device are read into an external electronic, optical or magnetic storage medium, e.g., a chip card. The chip card can then be introduced, e.g., into a writing and reading unit, which is associated with the medical engineering device and reads the data being stored on the chip card or generally on the storage medium. These data subsequently determine the clearing of exactly the modes of operation that shall be available on the medical engineering device. The medical engineering device may be a respirator and the modes of operation may be modes of respiration.

In a preferred embodiment of the process, the data are coded in the storage medium with a device-specific code, which may additionally be copy-protected. The writing and reading unit of the medical engineering device comprises means for decoding this code in order to subsequently read the data.

A time period for which a mode of operation shall be available may be specified for the individual available modes of operation. This may be performed, e.g., in the form of a time log which is kept for each mode of operation and by which time units during which the clearing of the mode of operation in question is performed can be debited. These time logs, which are kept in the storage medium, especially the chip card, can be filled up by an external writing unit, e.g., by the distributor of the chip cards or via the Internet.

The external storage medium is not bound to a special medical engineering device but can be used for a previously selected class of medical engineering devices of the same model, which are provided with a corresponding writing and reading unit.

In another embodiment, the data being stored in the storage medium can be transferred by the writing and reading unit which determines the clearing of the modes of operation that shall be available on the medical engineering device into a memory of the medical engineering device, or conversely, these data being stored in the memory of the medical engineering device can be transferred from the storage and reading unit into the storage medium.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1B:
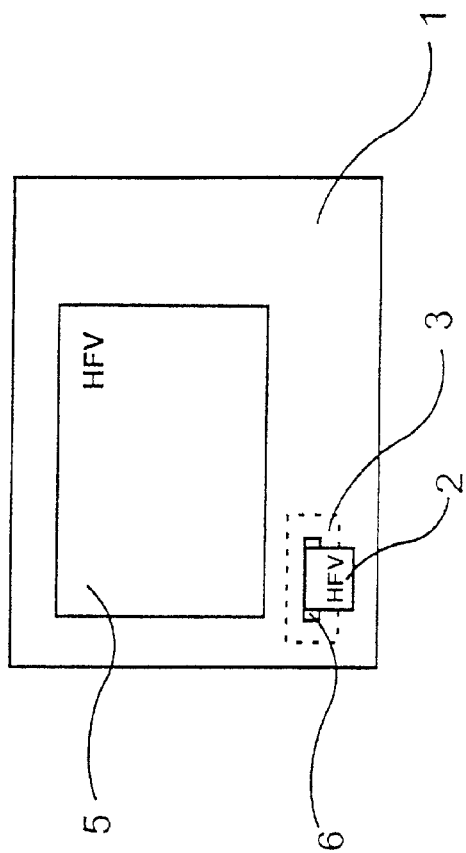
FIG. 1B is a schematic view showing a medical engineering device, particularly the respirator of FIG. 1A with the chip card introduced.
Figure 1A:
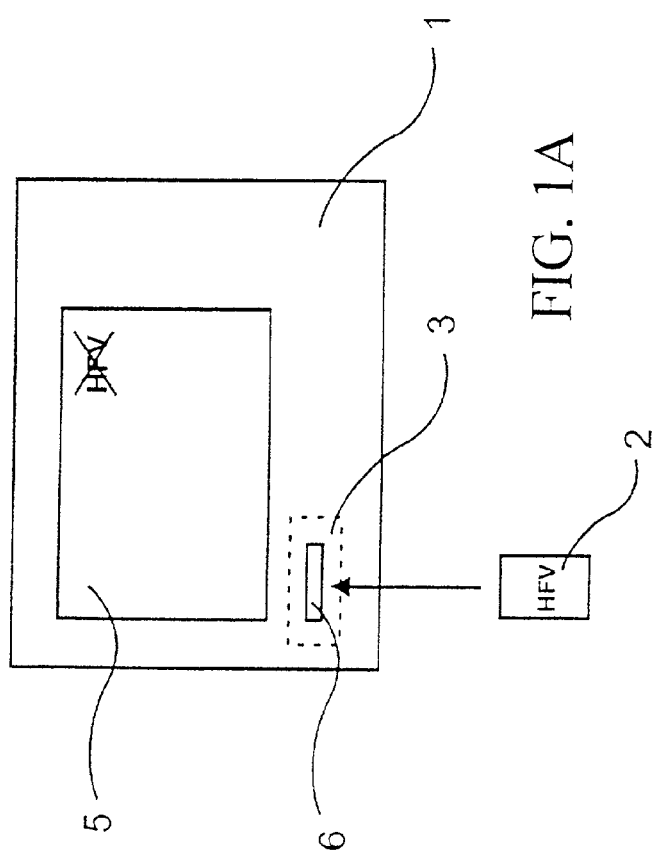
FIG. 1A is a schematic view showing a medical engineering device, particularly a respirator and a chip card located outside the respirator.

Referring to the drawings in particular, FIG. 1A shows a respirator 1 and a chip card 2 located outside the respirator 1. Data that specify HFV (High-Frequency Ventilation) as an available mode of respiration on the respirator 1 are present on the chip card 2. In FIG. 1A the writing and reading unit 3, which is associated with the respirator 1, has not yet read the data present on the chip card 2. HFV (High-Frequency Ventilation) is therefore displayed as unavailable on the display screen 5 of the modes of respiration, symbolized by "HFV" being crossed out. An arrow extends from the chip card 2 in the direction of a card slot 6, which is located on the respirator 1. The same arrangement as shown as in FIG. 1A is shown in FIG. 1B with the difference that the chip card 2 has been introduced into the card slot 6. In this position, the chip card 2 can be read by the writing and reading unit 3. The data present on the chip card 2 specify HFV (High- Frequency Ventilation) as an available mode of respiration. The data present on the chip card 2 determines the clearing of the mode of operation HFV (High-Frequency Ventilation). The mode of respiration HFV (High-Frequency Ventilation) is correspondingly no longer displayed as a crossed-out word on the display screen 5 of the modes of respiration. As long as the chip card 2 is in the card slot 6, the mode of respiration HFV (High-Frequency ventilation) is cleared. If the mode of respiration is needed on another device of the same model as the respirator 1, the chip card 2 is removed from the card slot 6 and is introduced into a comparable slot of the other device. Such another device with slot is not shown in FIG. 1.

Figure 2:
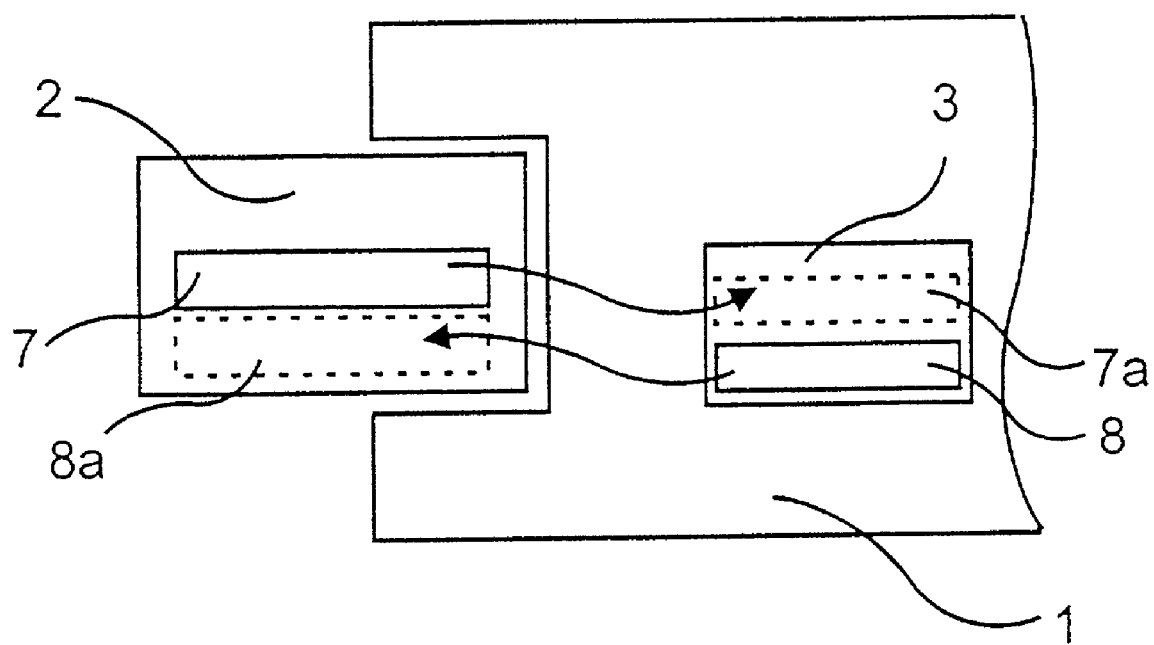
FIG. 2 is the respirator and with the chip card provided with a code.

FIG. 2 shows a respirator 1 with an identification number 8 as well as a chip card 2 with a code 7. The code 7 is copy-protected. If the chip card 2 is read by the writing and reading unit 3, the writing and reading unit 3 first downloads the code 7 from the chip card. The writing and reading unit 3 decodes the code 7 and also reads the other data present on the chip card 2. The downloading procedure is represented by an arrow that points from the code 7 present on the chip card 2 to the code 7a that is already present in the writing and reading unit 3 and is indicated by dotted lines. Conversely, the writing and reading unit 3 wires an identification number 8 of the respirator 1 on the chip card 2 after this has been read. The identification number 8 is stored on the chip card 2. The storage procedure is indicated by an arrow that points from the identification number 8 present on the respirator 1 to the identification number 8a that is already present on the chip card 2 and is indicated by broken lines.

The chip card 2 can thus be removed from the respirator 1 at any time, but no modes of respiration can be cleared by inserting the chip card 2 into another device because the code 7, which would first have to be decoded for this purpose, is no longer on the chip card 2 but in the respirator 1. The identification number 8a being stored on the chip card 2 is recognized by the writing and reading unit 3 and the code 7a is automatically reloaded from the writing and reading unit 3 onto the chip card 2 only when the chip card 2 is again introduced into the respirator 1. The code 7a is now again on the chip card 2, so that modes of respiration can also be cleared on other devices of the same model as the respirator 1 by inserting the chip card 2.

Figure 3:
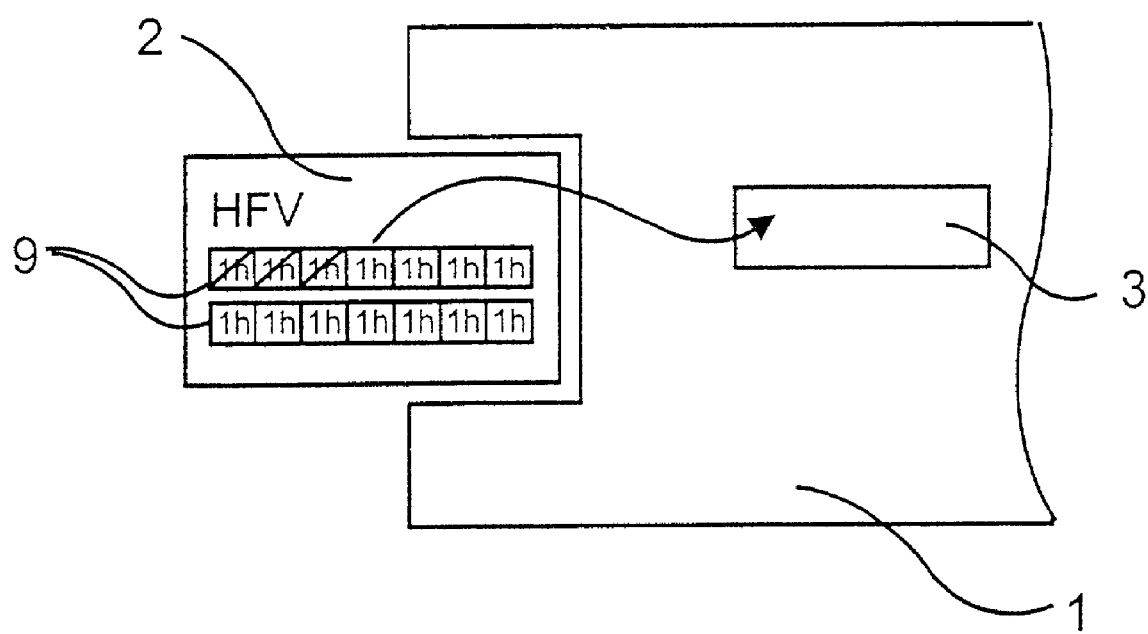
FIG. 3 is the respirator and the chip card provided with a time log.

FIG. 3 shows a respirator 1 and a chip card 2 provided with a time log 9 for the mode of respiration HTV (High-Frequency Ventilation). The chip card 2 is outside the respirator 1. However, it can be introduced into the respirator 1 and can also be removed from same. These two possibilities are indicated by two arrows, which extend from the chip card 2 to the writing and reading unit 3 and from the writing and reading unit 3 to the chip card 2. The time log 9 of the chip card comprises a total of 18 operating hours ("1 hr."), of which three operating hours ("1 hr.") have already been debited, characterized by three crossed-over fields of a total of 18 fields, all of which are provided with the label "1 hr. "

If the chip card 2 is introduced into the respirator 1 to clear the mode of respiration HFV (High-Frequency Ventilation), 3 operating hours are debited from the time log 9 by the writing and reading unit 3 corresponding to the operating time of the respirator 1 in the mode of respiration HFV (High-Frequency Ventilation).

While specific embodiments of the invention have been shown and described in detail to illustrate the application of the principles of the invention, it will be understood that the invention may be embodied otherwise without departing from such principles.

What is claimed is:

1. A process for clearing modes of operation on a respirator with the following steps:
   reading data that specify a number of different available modes of operation of the respirator into an external electronic, optical or magnetic storage medium, said data being encoded as a code in said storage medium;
   reading and encoding the data by a writing and reading unit associated with the respirator; and
   determining the clearing of the available modes of operation on the respirator based on the data read by the writing and reading unit, said data read into the storage medium specifying a time period during which a mode of operation is available for a particular mode of operation.

2. A process in accordance with claim 1, wherein the time period specified is present in the storage medium as a time log for each available mode of operation, from which time log time units during which the clearing of the mode of operation in question is performed can be debited.

3. A process in accordance with claim 2, wherein a time log kept in the storage medium is filled up by an external writing unit.

4. A process in accordance with claim 1, wherein the storage medium element is used for a previously selected class of respirators of the same model or type as the respirator.

5. A process in accordance with claim 1, wherein the data being stored in the storage medium can be transferred by the writing and reading unit into a memory of the respirator.

6. A process in accordance with claim 1, wherein data being stored in the memory of the respirator can be transferred by the writing and reading unit to the storage medium element.

7. A process in accordance with claim 1, wherein the storage medium is a chip card external to the respirator.

8. A process in accordance with claim 1, wherein the modes of operation are modes of respiration.

9. A respirator system, comprising:
   a respirator with a separate data storage medium element connection;
   a separate data storage medium element external to said respirator, the storage medium being any one of an electronic, optical or magnetic storage medium connectable to the respirator, the storage medium element having data encoded into a code that specifies a number of different available modes of operation on the respirator, the data and code also determining the clearing of the available modes of operation on the respirator, the data read into the storage medium specifying a time period during which a mode of operation is available for a particular mode of operation;
   a selective connection between the data storage medium element and the respirator, said data storage medium element being repetatively connectable to and disconnectable from the respirator by said selective connection;
   a writing and reading unit associated with the respirator reading and decoding the code from the data storage medium element; and
   a respirator processor clearing the available modes of operation on the respirator based on the reading and decoding of the data from the data storage medium element.

10. A system in accordance with claim 9, wherein the time period specified is present in the storage medium as a time log for each available mode of operation, from which time log time units during which the clearing of the mode of operation in question is performed can be debited.

11. A system in accordance with claim 10, wherein a time log kept in the storage medium is filled up by an external writing unit.

12. A system in accordance with claim 9, wherein the storage medium element is used for a previously selected class of respirators of the same model or type as the respirator.

13. A system in accordance with claim 9, wherein the data being stored in the storage medium can be transferred by the writing and reading unit into a memory of the respirator.

14. A system in accordance with claim 9, wherein data being stored in the memory of the respirator can be transferred by the writing and reading unit to the storage medium element.

15. A system in accordance with claim 9, wherein the storage medium element is a chip card external to the respirator and the modes of operation are modes of respiration.

* * * * *